(12) United States Patent
Saffell et al.

(10) Patent No.: US 7,651,597 B2
(45) Date of Patent: Jan. 26, 2010

(54) ELECTROCHEMICAL SENSOR

(75) Inventors: John R. Saffell, Stoke Charity (GB); Richard Smith, Braintree (GB); Darry H. Dawson, Braintree (GB)

(73) Assignee: Alphasense Limited, Essex (GB)

( * ) Notice: Subject to any disclaimer, the term of this patent is extended or adjusted under 35 U.S.C. 154(b) by 632 days.

(21) Appl. No.: 11/012,503

(22) Filed: Dec. 15, 2004

(65) Prior Publication Data
US 2005/0145493 A1 Jul. 7, 2005

(30) Foreign Application Priority Data
Dec. 16, 2003 (GB) ................... 0329103.6

(51) Int. Cl.
*G01N 27/26* (2006.01)
(52) U.S. Cl. ............... 204/415; 204/409; 204/400; 204/431
(58) Field of Classification Search ......... 204/412–432, 204/400, 409
See application file for complete search history.

(56) References Cited

U.S. PATENT DOCUMENTS

| | | | | |
|---|---|---|---|---|
| 4,280,505 A | * | 7/1981 | Dali et al. ............... | 600/354 |
| 5,298,146 A | * | 3/1994 | Braden et al. ........... | 204/406 |
| 5,650,054 A | | 7/1997 | Shen et al. | |
| 5,830,337 A | * | 11/1998 | Xu ......................... | 204/400 |
| 5,865,973 A | * | 2/1999 | Kiesele et al. .......... | 204/415 |
| 5,932,079 A | * | 8/1999 | Haupt et al. ............ | 204/415 |
| 5,980,709 A | | 11/1999 | Hodges et al. | |
| 6,193,865 B1 | | 2/2001 | Hodges et al. | |
| 7,166,201 B2 | * | 1/2007 | Wolf ....................... | 204/433 |
| 2002/0121438 A1 | | 9/2002 | Saffell et al. | |

FOREIGN PATENT DOCUMENTS

| | | | | |
|---|---|---|---|---|
| EP | 1154267 | | 11/2001 | |
| EP | 1336840 | | 8/2003 | |
| GB | 0239296 A2 | * | 9/1987 | ........... 204/415 |
| GB | 2 420 860 A | | 6/2005 | |

OTHER PUBLICATIONS

UK Patent Office Search Report GB0427300.9, Apr. 21, 2005.
European Patent Office Search Report EPP290113, Apr. 22, 2005.

* cited by examiner

*Primary Examiner*—Nam X Nguyen
*Assistant Examiner*—Bach T Dinh
(74) *Attorney, Agent, or Firm*—Wolf, Greenfield & Sacks, P.C.

(57) ABSTRACT

A dual gas sensor is described, having first and second working electrodes separated by a gas impermeable portion. The electrodes are preferably located on a gas permeable polymer support, with the gas impermeable portion being formed by compression of the permeable support. The sensor may also include one or more filters for location adjacent the electrodes to filter certain gases from the air. The preferred sensor is able to detect carbon monoxide and hydrogen sulfide. The sensor housing is formed with four connection pins, allowing a standard sensor housing to be used for dual sensors as well as single sensors having a dummy pin.

12 Claims, 7 Drawing Sheets

Reservoir Assembly (Exploded)

Fig.6a

Reservoir Assembly

Fig.6b

Base + Reservoir Assembly

ELECTROCHEMICAL SENSOR

FIELD OF THE INVENTION

The present invention relates to an electrochemical sensor. In particular, but not exclusively, the invention relates to a gas sensor which may be used to detect two different gases.

BACKGROUND OF THE INVENTION

Electrochemical sensors for the measurement of gas concentrations are well known. Working, counter, and reference electrodes are connected through a potentiostat circuit, the main purpose of which is to set the bias potential of the working electrode through the reference electrode potential.

The working electrode (also called the sensing electrode) is designed to optimise the oxidation or reduction of the gas to be measured. This electrode allows the gas to come in contact with both electrocatalyst and electrolyte to create a three-phase interface of gas, liquid and solid. The other two electrodes in the cell, the counter electrode and the reference electrode usually have a similar chemical composition to the working electrode. Oxidation or reduction at the working electrode generates a current that is generally linearly proportional to the amount of gas oxidised or reduced; this current is therefore also proportional to the concentration of the gas at the electrode.

The cell electrolyte provides ionic electrical contact between the electrodes, usually with the aid of hydrophilic separators to allow capillary transport of the electrolyte.

The counter electrode balances the reaction of the working electrode—if the working electrode oxidises the gas, then the counter electrode must reduce some other molecule to generate an equivalent current, in the opposite sense. For example, where carbon monoxide will be oxidised on the working electrode, oxygen will usually be reduced on the counter electrode. Unlike the working electrode, the counter electrode potential is allowed to vary. The counter electrode potential in clean air is close to the working electrode, but as current is demanded from the counter electrode, the potential increases, so the secondary responsibility of the potentiostat circuit is to ensure that adequate current is fed to the counter electrode and that the counter electrode can operate at its preferred potential.

An important feature of conventional sensors is that certain gases may interfere with the desired working of the sensor. For example, in a sensor intended to measure carbon monoxide concentration, hydrogen sulfide may also react at the working electrode and generate a current indistinguishable from that generated by carbon monoxide. Particular interferents will depend on the particular form of sensor and the intended gas to be measured; the skilled person will be aware of these. To reduce such interference, it is generally necessary to isolate the sensor from the interferent gas; for example, carbon monoxide sensors are typically fitted with 'scrubbers', or chemical filters which allow carbon monoxide to pass but which prevent hydrogen sulfide from reaching the working electrode. While this arrangement is generally effective, this does mean that separate sensors are necessary to detect separate gases which may otherwise interfere with one another. This will increase the size and cost of any apparatus which requires sensors to detect multiple gases.

SUMMARY OF THE INVENTION

The present invention provides, in one aspect, a sensor which may be used to detect two different gases.

According to a first aspect of the present invention, there is provided an electrochemical sensor comprising first and second working electrodes, the electrodes being located on a gas permeable support, the sensor having a gas impermeable portion separating the first and second working electrodes.

This arrangement allows the first and second working electrodes to be configured to detect different gases; the permeable support permits gases to contact the electrodes while the impermeable portion prevents or restricts gases from passing from one electrode, or from the area above one electrode, to the other. This serves to reduce the risk that a gas at one electrode will also be detected at the other electrode. The electrodes may in certain embodiments be located on separate supports, but in preferred embodiments they are located on a common support. Location of the electrodes on a common permeable support allows for ease of manufacture and reduced size compared with alternative sensors which require separate electrodes and separate supports to prevent gas interference.

By 'permeable support' is meant a support on which the electrode is located which allows diffusion of the gas to be detected therethrough. By 'impermeable portion' is meant a portion which prevents or restricts diffusion of the gas to be detected therethrough. It is not considered necessary that the impermeable portion completely prevents diffusion of the gas, only that the impermeable portion has a reduced permeability as compared to the permeable support, such that diffusion of gas between electrodes is reduced sufficiently to permit the first and second electrodes to be used to detect different gases.

The support may comprise a porous polymer; conveniently a fluoropolymer, and preferably PTFE. The polymer may be an expanded polymer, such as ePTFE, which comprises a structure of nodes interconnected by fibrils. For example, GORE-TEX® may be used. The polymer may alternatively be sintered, to provide a permeable structure.

The impermeable portion is conveniently integral with the support, and is preferably comprised of the same material as the support. The impermeable portion is preferably treated to render it impermeable. In preferred embodiments of the invention, the impermeable portion is placed under compression to render it impermeable; such treatment will generally close or reduce pores and openings within a porous polymer, thereby rendering it impermeable. This compression may be applied during manufacture of the support and portion, and is preferably applied and/or maintained during use of the sensor. For example, the sensor may comprise a contact portion arranged to apply compression to the impermeable portion in order to render it impermeable. Again this arrangement is intended to provide a support which is relatively inexpensive and simple to manufacture.

Preferably at least one of the working electrodes comprises platinum;
    conveniently platinum black. Platinum black will typically be mixed with a binder, for example microparticulate PTFE. Alternatively, or in addition, a platinum alloy may be used; for example, a platinum/ruthenium alloy. The first and second working electrodes may comprise the same material, or may comprise different materials. The particular choice of materials for the electrodes will depend on the purpose to which the sensor is to be put.

The sensor may further comprise one or more filters located adjacent the first or second working electrodes. The filters are preferably selected to filter interfering gases from the gas reaching the electrodes; the person of skill in the art will be aware of suitable filter materials for particular gases. For example, activated carbon may be used to filter hydrogen sulfide. Preferably the sensor comprises first and second filters located adjacent the first and second working electrodes respectively. The first and second filters are preferably comprised of different materials, to filter different gases. In certain embodiments, one of the filters may be inactive or may not be used; for example, where the sensor is a combined carbon monoxide/hydrogen sulfide sensor, it is only necessary to filter hydrogen sulfide from the carbon monoxide electrode. The second filter may therefore be inactive or removed, although it is preferred that an inactive filter is used rather than no filter in order to maintain an even pressure on the electrode assembly. Preferably the two filters are separated by an impermeable member. For example, the impermeable member may comprise a raised ridge or the like, separating the filters and preventing gas exchange. Use of a raised ridge is also preferred in certain embodiments, since this may also be used to exert compression on the impermeable portion of the support member.

Preferably the sensor further comprises a cap. The cap may comprise portions within which filters may be located, and may further comprise a raised ridge or the like for separating the filters. The cap will include pores or other openings to allow gas access to the filters and electrodes. A peripheral sealing means, for example, an O-ring, may also be present, to seal the sensor assembly.

Preferably the sensor further comprises an electrolyte reservoir. The reservoir is preferably located within a base of the sensor. The base conveniently carries pins for connection to the electrodes of the sensor, to allow the sensor to be connected into a circuit. Preferably the base includes an opening into which the reservoir and electrolyte contained therein extend. This arrangement allows reservoir volume to be maximised while still maintaining a relatively compact sensor arrangement. The reservoir may be provided as a separate container which fits into the opening provided in the base.

The base of the sensor preferably comprises four pins for connection to the electrodes of the sensor. Two pins are for connection to the first and second working electrodes, respectively, while the third and fourth pins provide connections to common reference and counter electrodes. This arrangement also allows for compatibility with single gas sensors, which may be constructed with four equivalent pins of which one is a 'dummy', and does not connect to a second working electrode.

This universal four-pin construction allows a gas detector manufacturer to design a single circuit board that accepts carbon monoxide, hydrogen sulfide, or dual carbon monoxide/hydrogen sulfide sensors, reducing manufacturing costs.

According to a further aspect of the invention, therefore, there is provided an electrochemical sensor comprising a working electrode, a reference electrode, and a counter electrode, the sensor further comprising a base portion having three pins connected to respective electrodes, and a fourth dummy pin which is not connected to an electrode.

Also provided is an electrochemical sensor comprising first and second working electrodes, a reference electrode, and a counter electrode, the sensor further comprising a base portion having four pins connected to respective electrodes.

A still further aspect of the invention provides an electrochemical sensor having a base portion, and an electrolyte reservoir located adjacent the base portion, the base portion further comprising an opening into which the reservoir and electrolyte contained therein extend.

BRIEF DESCRIPTION OF THE DRAWINGS

These and other aspects of the present invention will now be described, by way of example only and without limitation, with reference to the accompanying drawings, in which.

DETAILED DESCRIPTION OF THE DRAWINGS

Figure 1:
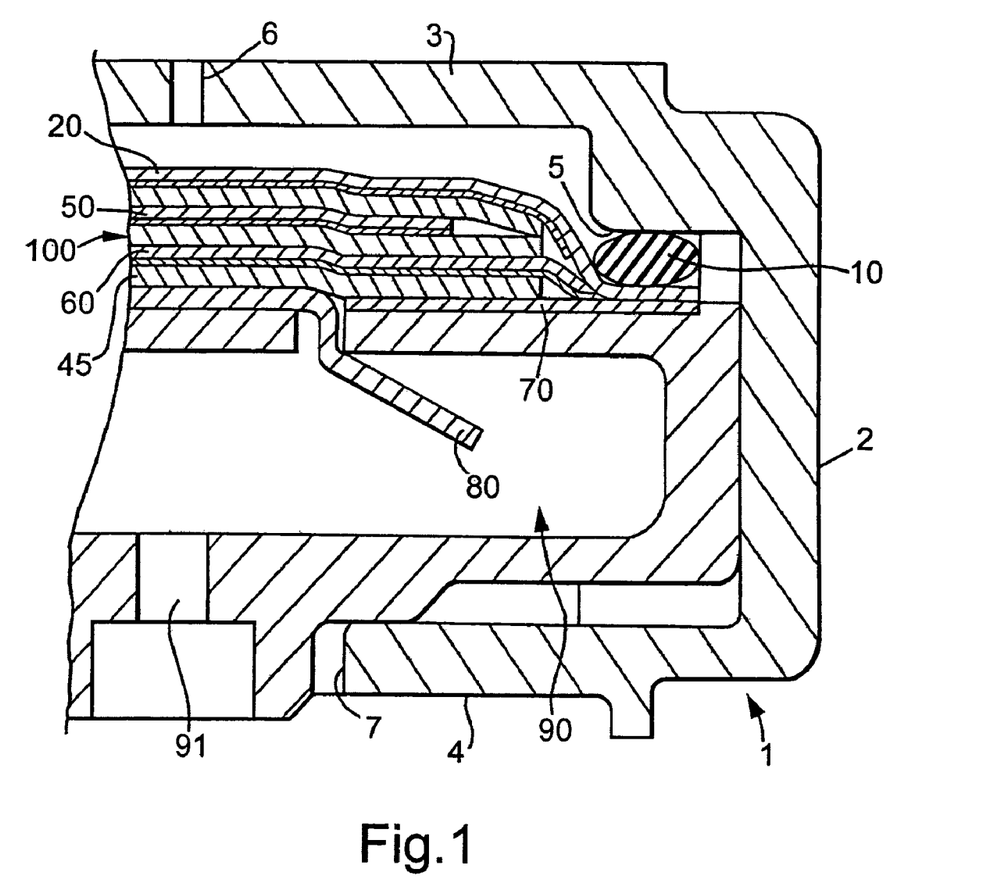
FIG. 1 shows a sectional view of a conventional electrochemical sensor, useful for understanding of the present invention.

FIG. 1 shows a simplified sectional view of a conventional electrochemical sensor. The sensor comprises a generally cylindrical sensor casing 1, made of a plastics material such as polycarbonate or polysulfone, in which is housed an electrolyte reservoir 90, an electrode stack assembly 100, and a wick 80 of glass fibre, a hydrophilic non-conductive electrolyte transporting material, which functions to transport electrolyte by capillary action, extending into the reservoir 90 for contact with electrolyte therein.

Sensor casing 1 has a cylindrical side wall 2 and generally planar top and base portions 3 and 4. The top portion 3 has a stepped configuration and includes an annular shoulder portion 5 around the periphery, A central circular capillary opening 6 passes through the top portion 3 which functions to permit gas passage to the interior of the casing. The bottom portion 4 includes an opening 7 which provides access to an opening 91 formed in the reservoir 90 to enable injection of electrolyte during manufacture.

The casing 1 is conveniently of two part construction for assembly purposes. The electrode stack 100 comprises an annular stack base 70 of polyethylene or similar polymer. This is followed by a circular separator disc 45 made of glass fibre which is a hydrophilic, non-conductive material permeable to the electrolyte which functions to transport electrolyte by capillary action.

A counter electrode 60 follows, which comprises a catalytic layer of material such as platinum black mixed with PTFE binder sintered at elevated temperature to give a porous binder/catalyst material which is then bonded to a hydrophobic porous PTFE support (such as GORE TEX®).

A further separator disc 45 separates the counter electrode 60 from a similarly-constructed reference electrode 50, which in turn is followed by another separator disc 45 and a working electrode 20 of similar construction. An O ring 10 is located at the top of the assembly, which seals the sensor and brings the various components of the electrode stack 100 into close contact with one another. Also present, but not shown in FIG. 1, are a number of platinum strips which serve to connect each electrode to a corresponding terminal pin provided on the base of the sensor. Three such pins and strips will typically be provided.

Figure 2:
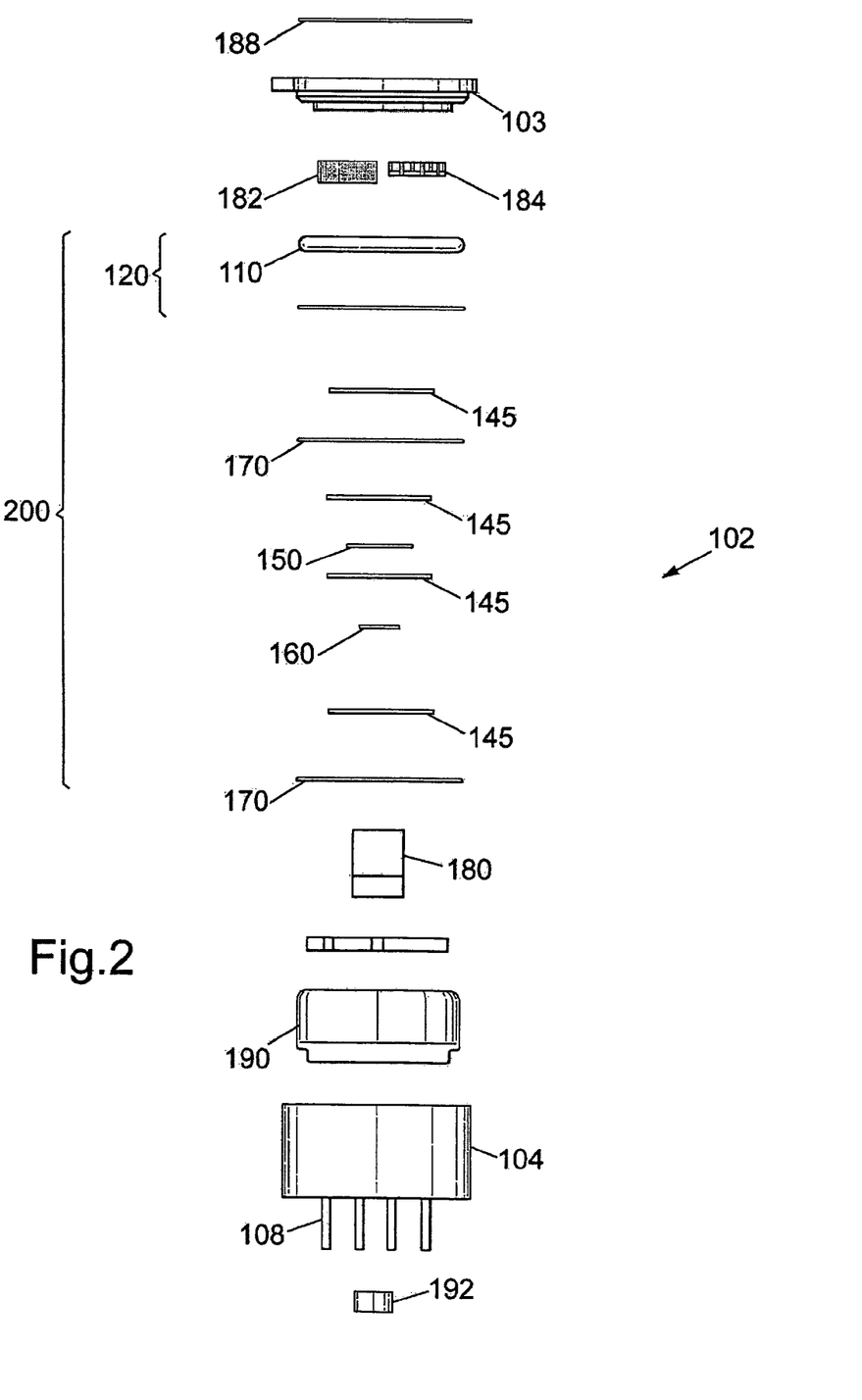
FIG. 2 shows an exploded view of an electrochemical sensor in accordance with an embodiment of the present invention.
Figure 3:
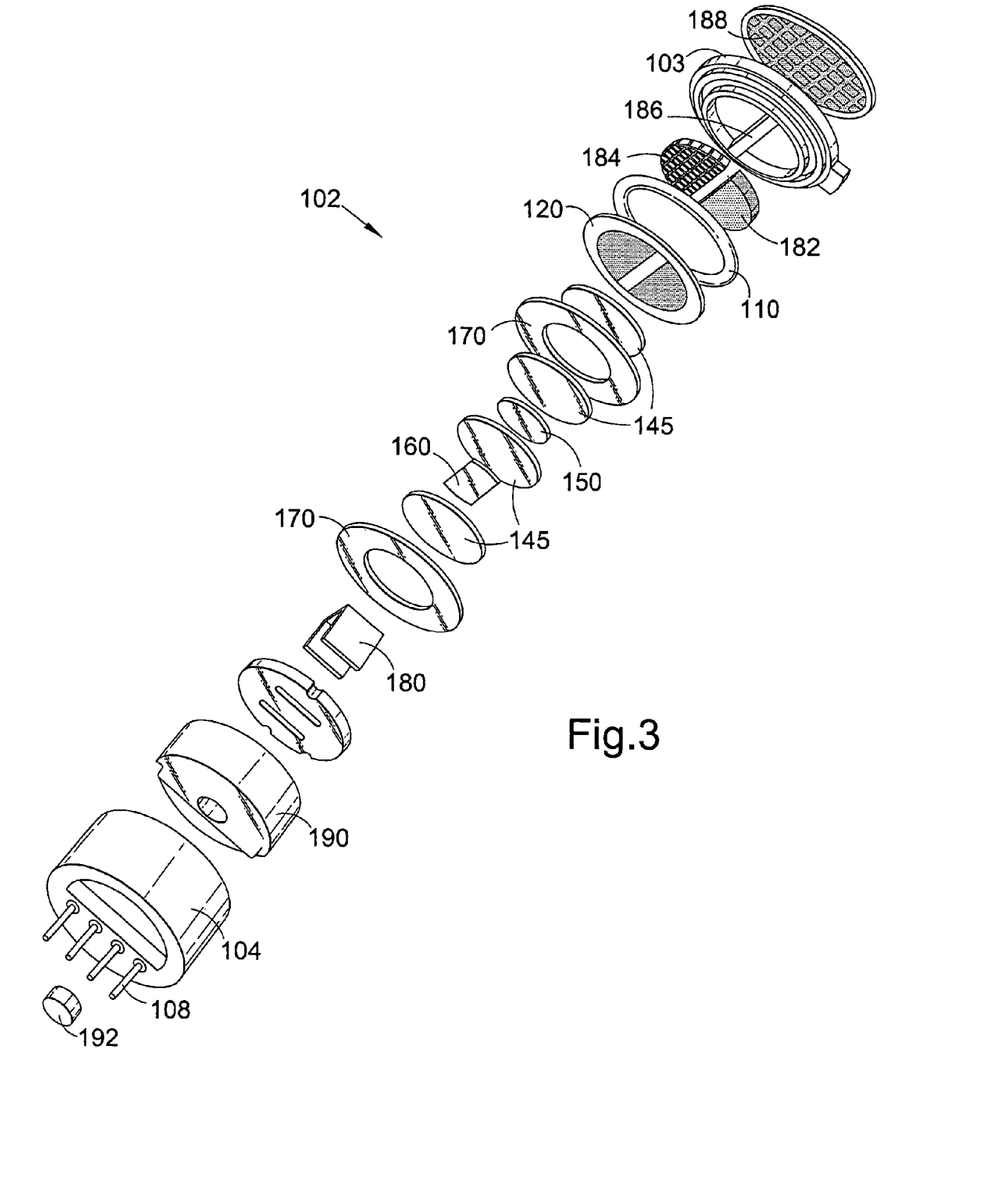
FIG. 3 shows a perspective exploded view of the sensor of FIG. 2.

The sensor of FIG. 1 includes a single working electrode 20, and so is able to be used to detect only a single gas. FIGS. 2 and 3 show exploded and exploded perspective views of a sensor in accordance with an embodiment of the present invention, which includes two working electrodes.

The sensor 102 of FIGS. 2 and 3 includes similar components to that of FIG. 1. From the bottom of FIG. 2 upwards, the sensor 102 includes a reservoir bung 192 for sealing the reservoir 190, which is mounted within a base portion 104. The base portion 104 includes four pins 108, rather than the conventional three.

Extending into the reservoir 190 is a hydrophilic wick 180, above which is mounted the electrode stack 200. The stack 200 is similar in construction to the stack 100 of FIG. 1, including a hydrophobic annulus 170, typically of polyethylene, and a series of hydrophilic wicks 145 separating counter, reference, and working electrodes 160, 150, 120. The working electrode 120 is, however, of somewhat different construction to that of FIG. 1, as will be described further below.

Above the working electrode 120 is provided an O ring 110 to compress the stack 200, and a pair of filters 182, 184. One of these filters 182 comprises activated carbon or similar chemical scrubbing material to, for example, remove hydrogen sulfide from gas passing through the filter, while the other filter 184 is inactive or not included, and allows all gas to pass.

Closing the sensor assembly is a top portion 103, which includes a central raised ridge 186 which separates the two filters 182, 184. Mounted on the top portion is a dust filter 188, to prevent dust and other foreign objects from entering the sensor.

Figure 4:
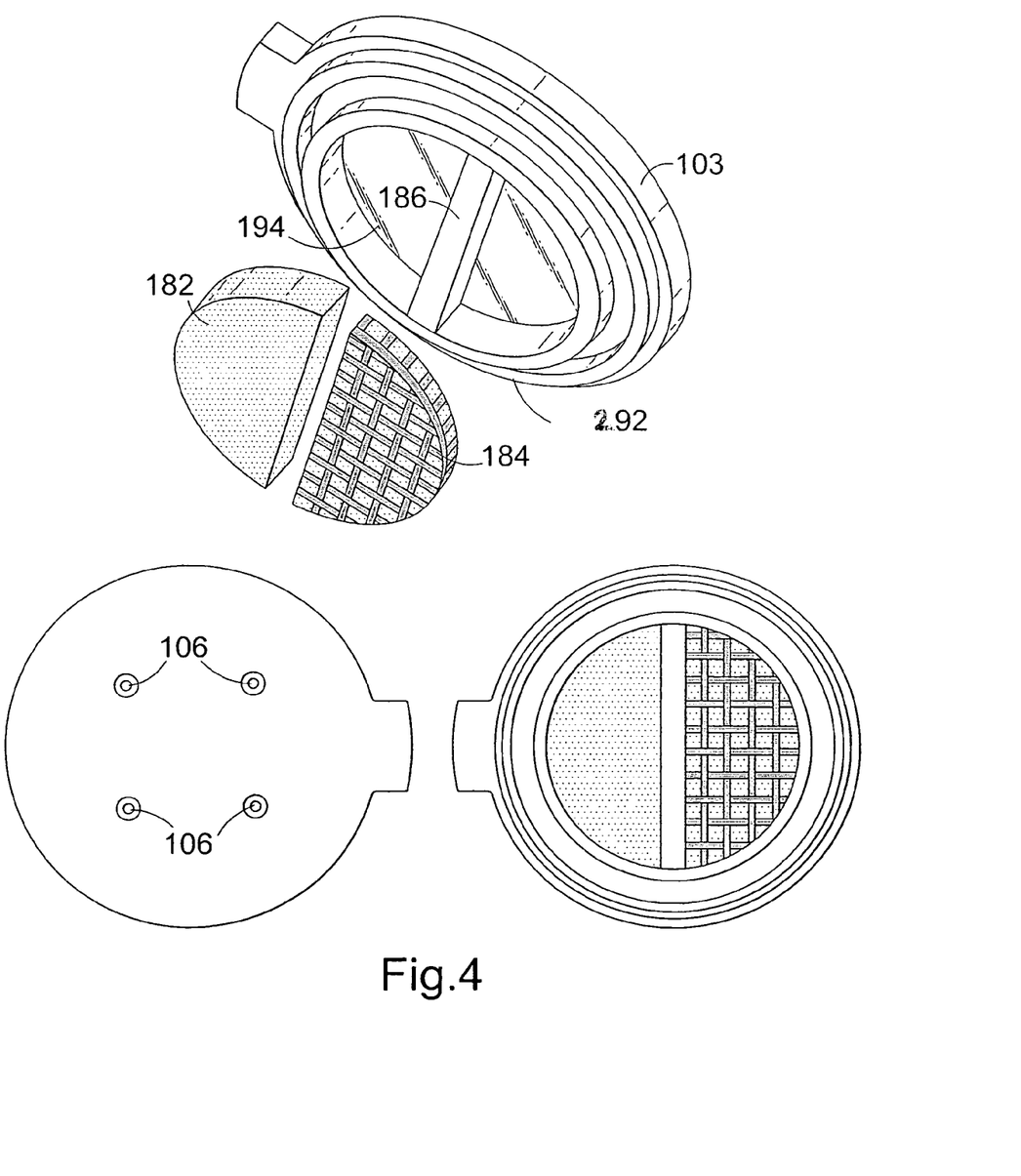
FIG. 4 shows perspective, top, and bottom views of the cap and filters of the sensor of FIG. 2.

FIG. 4 shows the top portion 103 and filters 182, 184 in more detail. The filters 182, 184 are semicircular and fit into recesses 292, 194 defined in the top portion 103 separated by the raised ridge 186. The use of an inactive filter 184, rather than no filter, is preferred since it maintains an even pressure on the electrode stack 200 when the sensor is assembled (although construction without the inactive filter is within the scope of the invention). The figure also shows a number of capillary holes 106 in the cap portion; preferably at least two are present.

Figure 5:
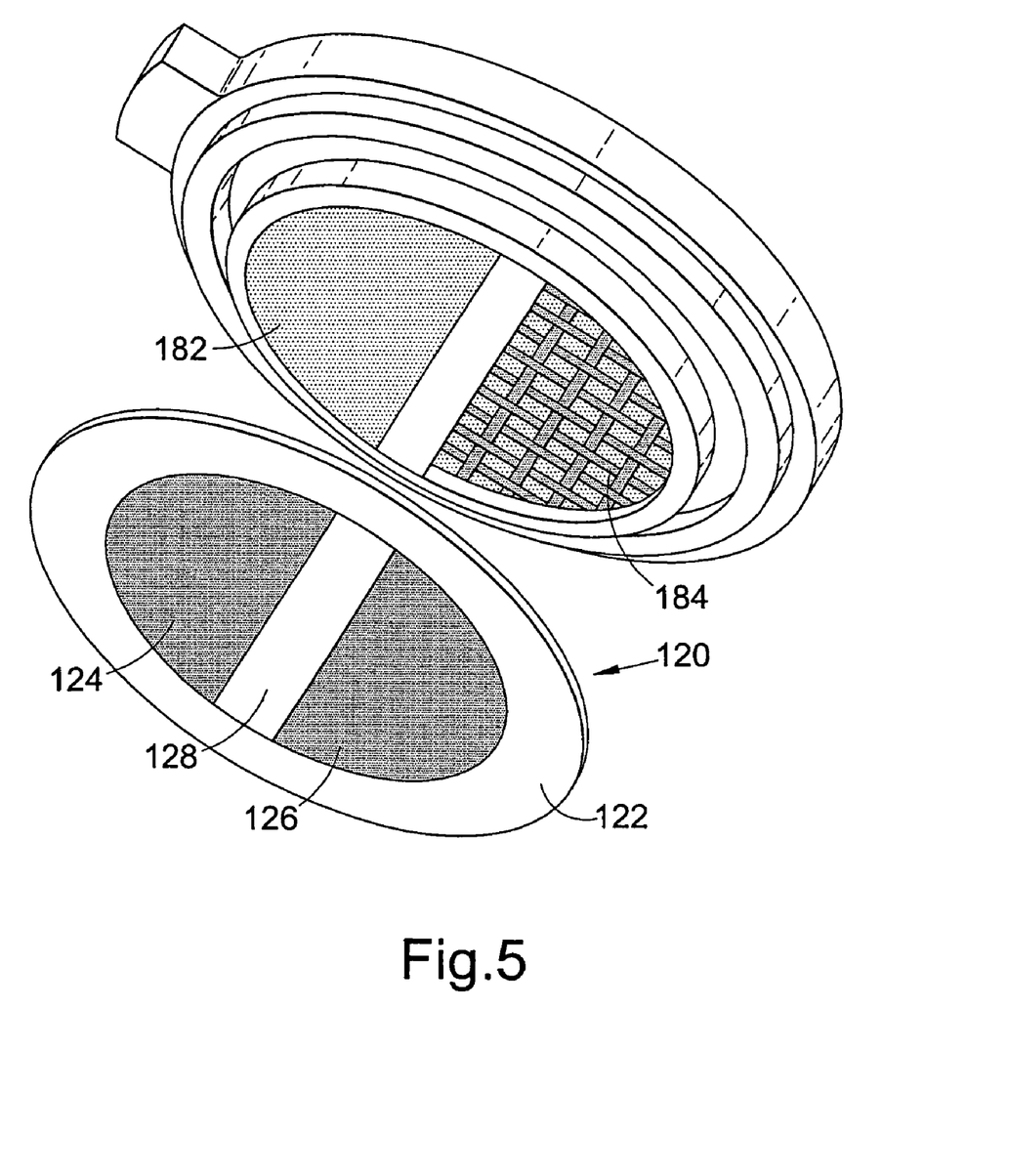
FIG. 5 shows a perspective view of the cap and working electrodes of the sensor of FIG. 2.

FIG. 5 shows the top portion 103 and filters 182, 184 in combination with the working electrode 120. The working electrode 120 comprises a permeable PTFE support 122 on which are located first and second electrodes 124, 126, in the form of platinum black or a platinum alloy respectively mixed with particulate PTFE. Each of the electrodes 124, 126 is located adjacent a respective one of the filters 182, 184. The electrodes 124, 126 are separated from one another by a central portion 128 of the support 122, which in use is located adjacent the raised ridge 186 of the top portion 103. Portion 128 is compressed or otherwise treated during manufacture of the electrode 120, and/or compressed by the pressure exerted on the stack by the ridge 186, to reduce the permeability of that portion of the support. When the sensor is assembled, the raised ridge 186 fits tightly next to the central portion 128 of the support. This reduced permeability portion, in combination with the raised ridge, serves to prevent or reduce gas passing between the first and second working electrodes which could otherwise affect the sensor operation. The sensor can therefore be used to detect two otherwise interfering gases; for example, carbon monoxide and hydrogen sulfide.

Figure 6A:
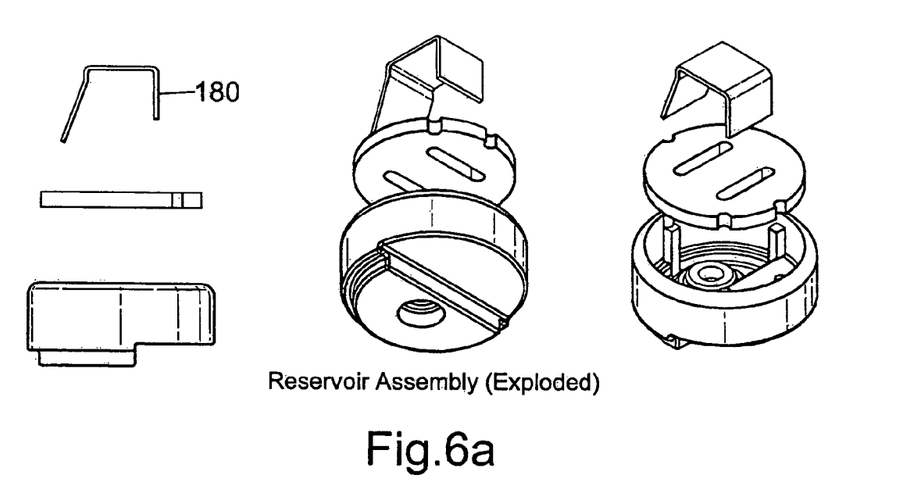
FIG. 6 shows several views of the base and reservoir assembly of the sensor of FIG. 2.
Figure 6B:
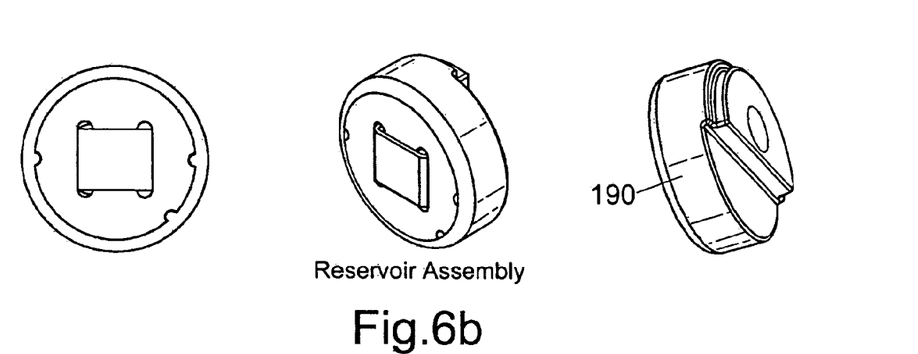
Figure 6C:
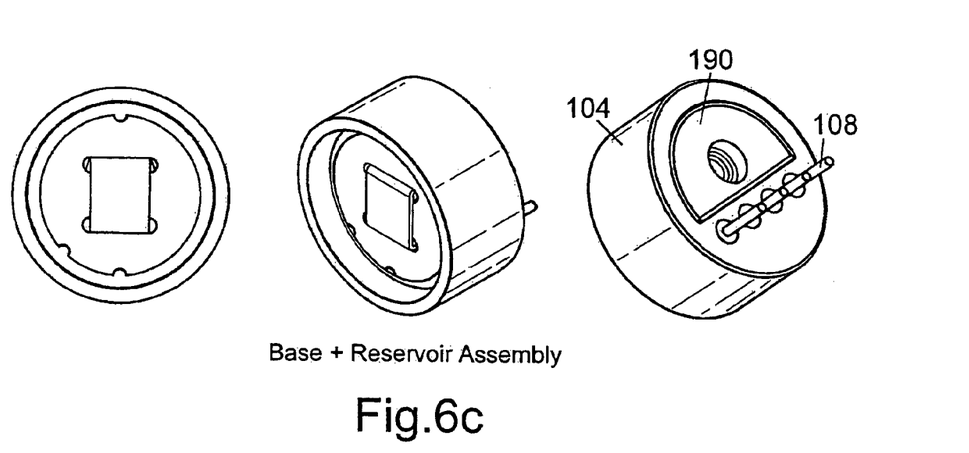
Figure 7A:
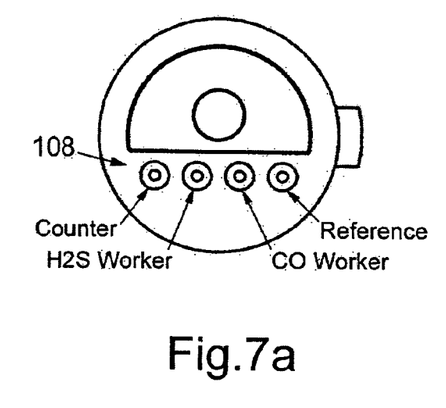
FIG. 7 shows bottom views of a dual gas sensor, and three individual gas sensors.
Figure 7B:
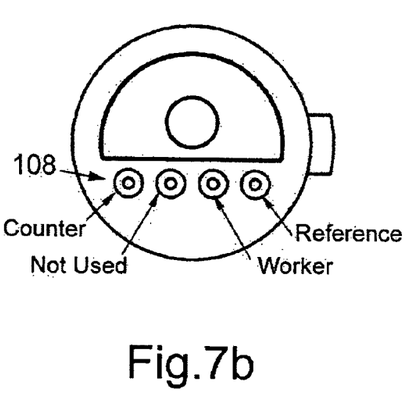
Figure 7C:
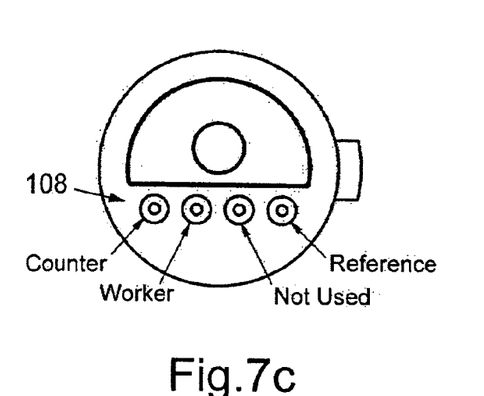
Figure 7D:
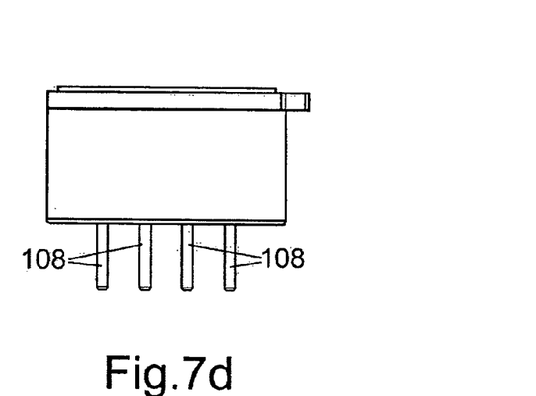

Referring now to FIG. 6, this shows the base portion 104 and reservoir assembly 190 of the sensor in more detail. It can be seen that the base portion 104 includes a large aperture through which a portion of the reservoir 190 extends; the reservoir is constructed so that this portion which extends through the aperture also contains some of the electrolyte when in use. This arrangement increases the effective volume of electrolyte without increasing the overall size of the sensor. The lower wall of the reservoir is flush with the lower wall of the base portion 104.

FIG. 7 shows four forms of sensor. FIG. 1a shows a dual gas sensor as herein described, which includes four pins 108; from left to right, these are connected to the counter electrode, the first worker electrode, the second worker electrode, and the reference electrode. FIG. 1b shows a single gas sensor, in this example carbon monoxide, which also includes four pins. Of these, the second pin (from left to right) is not connected to any electrode, while the other three pins are connected as for the dual gas sensor. FIG. 7c shows a hydrogen sulfide single gas sensor, in which the third pin is not connected. FIG. 7d shows a side view of any of these types of sensor. This construction allows any one of these sensors to be used in a common circuit board with the same connections for each. This flexibility allows for more standardisation and reduced cost for all three types of sensor. Sensors to measure other gases can be constructed in the four-pin format using either the carbon monoxide or the hydrogen sulfide pin configuration, but possibly without the cost savings of a universal circuit board.

Experiment

An experiment was performed to demonstrate the effectiveness of the impermeable barrier. Sixty four dual sensors as herein described were tested. 400 ppm of CO and 20 ppm of $H_2S$ were sequentially applied to both electrodes. The generated current was measured. The table below lists the results, with sensitivity specified as nA/ppm, as both the mean sensitivity and the standard deviation. Without a filter and diffusion barrier the $H_2S$ sensitivity on the CO electrode would be about 190 nA/ppm, but with the filter and barrier, it is only 1.2 nA/ppm.

| Dual sensor: CO, $H_2S$ | Mean | Standard Deviation |
|---|---|---|
| CO electrode | | |
| CO sensitivity (nA/ppm) | 47.5 | 3.3 |
| $H_2S$ sensitivity (nA/ppm) | 1.2 | 2.1 |
| $H_2S$ electrode | | |
| $H_2S$ sensitivity (nA/ppm) | 121.3 | 5.4 |
| CO sensitivity (nA/ppm) | 0.4 | 0.2 |

The foregoing is for illustrative purposes only, and it will be understood that various modifications and variations may be made to the device described herein without departing from the scope of the invention.

The invention claimed is:

1. An electrochemical gas sensor comprising first and second working electrodes, the electrodes being located on a gas permeable support common to said electrodes, the support having an integral gas impermeable portion separating the first and second working electrodes, and further including a contact portion arranged to apply compression to the impermeable portion to render it impermeable.

2. The sensor of claim 1 wherein the support comprises a porous polymer.

3. The sensor of claim 1 wherein the support comprises a fluoropolymer.

4. The sensor of claim 1 further comprising one or more filters located adjacent the first or second working electrodes.

5. The sensor of claim 1 comprising first and second filters located adjacent the first and second working electrodes respectively.

6. The sensor of claim 5 wherein one of the filters is inactive.

7. The sensor of claim 5 wherein the first and second filters are separated by an impermeable member.

8. The sensor of claim 1 further comprising a cap.

9. The sensor of claim 1 further comprising an electrolyte reservoir.

10. The sensor of claim 9 wherein the reservoir is located within a base of the sensor.

11. The sensor of claim 10 wherein the base carries pins for connection to the electrodes of the sensor, to allow the sensor to be connected into a circuit.

12. The sensor of claim 1 comprising a base having four pins for connection to the electrodes of the sensor.

* * * * *